(12) United States Patent
Jörgensen

(10) Patent No.: US 8,029,153 B2
(45) Date of Patent: Oct. 4, 2011

(54) COMBINATION AROMATIC NEBULIZING DIFFUSER AND COLOR LIGHT SET ASSEMBLY

(75) Inventor: Carsten Jörgensen, Kastanienbaum (CH)

(73) Assignee: Ming Jen Hsiao, Miaoli (TW)

( * ) Notice: Subject to any disclaimer, the term of this patent is extended or adjusted under 35 U.S.C. 154(b) by 186 days.

(21) Appl. No.: 12/573,875

(22) Filed: Oct. 5, 2009

(65) Prior Publication Data

US 2011/0080724 A1 Apr. 7, 2011

(51) Int. Cl.
*F21V 33/00* (2006.01)
(52) U.S. Cl. ............... 362/96; 362/101; 362/253
(58) Field of Classification Search .......... 362/96, 362/101, 253, 294, 318; 239/338
See application file for complete search history.

(56) References Cited

U.S. PATENT DOCUMENTS

| | | | | |
|---|---|---|---|---|
| 3,749,901 | A * | 7/1973 | Clough | 362/101 |
| 6,676,271 | B2 * | 1/2004 | Kohn et al. | 362/96 |
| 6,877,883 | B2 * | 4/2005 | Lau Ting Yup et al. | 362/318 |
| 2005/0116059 | A1 * | 6/2005 | Lin | 239/289 |
| 2011/0079660 | A1 * | 4/2011 | Jorgensen | 239/338 |

* cited by examiner

*Primary Examiner* — Y My Quach Lee
(74) *Attorney, Agent, or Firm* — Chun-Ming Shih

(57) ABSTRACT

An aromatic nebulizing diffuser and color light set assembly includes a fluid container, a base panel carrying two electric fans beneath the fluid container for drawing in outside air, an oscillator for causing automation of an aromatic fluid in the fluid container, a color light set for emitting color light upwardly toward the inside of the fluid container, a power adapter mounted on the base panel for providing the electric fans, the oscillator and the color light set with the necessary working voltage, a shell supporting the fluid container on a flat surface, light guide tubes mounted in the fluid container for condensing emitted color light from the color light set into vertically extending color light beams, and a slotted cover covering the top side of the fluid container.

10 Claims, 5 Drawing Sheets

COMBINATION AROMATIC NEBULIZING DIFFUSER AND COLOR LIGHT SET ASSEMBLY

BACKGROUND OF THE INVENTION

1. Field of the Invention

The present invention relates to an aromatic nebulizing diffuser and more particularly, to a combination aromatic nebulizing diffuser and color light set assembly that provides a colorful lighting effect when causing atomization of an aromatic fluid.

2. Description of the Related Art

Commercial aromatic nebulizing diffusers commonly use oscillator means to generate a high ultrasonic energy for causing atomization of an essential oil. These aromatic nebulizing diffusers do not produce any visual lighting effects. There are aromatic nebulizing diffusers with a lamp arranged therein. However, because the housing or outer shell does not admit light, people cannot see the floating of the generated fine mid in the housing or outer shell.

Further, a conventional aromatic nebulizing diffuser with a lamp simply uses a light emitting device to emit light. The lighting of the light emitting device is monotonous, insufficient to attract people's eyes.

Further, regular aromatic nebulizing diffusers commonly use screws to affix component parts together, complicating mounting and dismounting procedures. After a long use, the inside wall of the aromatic nebulizing diffuser may be covered with a layer of dirt. It takes much time and labor to practice a cleaning work.

Further, regular aromatic nebulizing diffusers commonly have a narrow flow passage for guiding out the generated fine mist of atomized aromatic fluid molecules. Thus, the amount of the generated fine mist of atomized aromatic fluid molecules being carried out of the housing or outer shell is limited.

Further, during operation of the oscillator to cause atomization of the aromatic fluid, the aromatic fluid may be causes to fly out of the housing or outer shell, causing contamination.

SUMMARY OF THE INVENTION

The present invention has been accomplished under the circumstances in view. It is main object of the present invention to provide a combination aromatic nebulizing diffuser and color light set assembly, which emits color light to produce a visual lighting effect when generating a fine mist of atomized aromatic fluid molecules.

It is another object of the present invention to provide a combination aromatic nebulizing diffuser and color light set assembly, which utilizes light guide tubes to condense color light emitted from a color light set into color light beams when generating a fine mist of atomized aromatic fluid molecules, providing a visual lighting effect.

It is still another object of the present invention to provide a combination aromatic nebulizing diffuser and color light set assembly, which causes automation of an aromatic fluid efficiently.

It is still another object of the present invention to provide a combination aromatic nebulizing diffuser and color light set assembly, which facilitates mounting, dismounting and cleaning works.

It is still another object of the present invention to provide a combination aromatic nebulizing diffuser and color light set assembly, which prevents splashing of the aromatic fluid when causing automation of the aromatic fluid.

To achieve these and other objects of the present invention, a combination aromatic nebulizing diffuser and color light set assembly comprises a base panel, which comprises a plurality of air vents cut through top and bottom sides thereof, at least one electric fan mounted on the top side of the base panel corresponding to the air vents for drawing in outside air, a fluid container, which comprises a bottom wall, an upright peripheral wall, a fluid chamber surrounded by the bottom wall and the upright peripheral wall for holding an aromatic fluid, at least one air conduit suspending in the fluid chamber, each air conduit having an air inlet facing one said electric fan for guiding in currents of air from the associating electric fan and an air outlet in air communication with the space in the fluid chamber of the fluid container above the aromatic fluid contained, an opening cut through said bottom wall and a plurality of through holes cut through the bottom wall, an oscillator mounted in the opening of the fluid chamber for generating an oscillating energy to cause automation of the aromatic fluid in the fluid chamber, a color light set, which comprises a circuit board affixed to the bottom wall of the fluid container and a plurality of light emitting devices electrically connected to the circuit board and respectively mounted in the through holes on the bottom wall of the fluid container, a power adapter mounted on the base panel and electrically connected with the at least one electric fan, the oscillator and the circuit board of the color light set to provide the necessary working voltage to the at least one electric fan, the oscillator and the color light set, a shell, which has a top edge stopped against the bottom wall of the fluid container and a plurality of legs downwardly extended from a bottom side thereof in four corners for positioning on a flat surface to hold the fluid container above the flat surface, a plurality of light guide tubes vertically positioned in the fluid chamber of the fluid container and adapted to condense emitted light from the light emitting devices into a respective light beam, and a cover, which is covered on the fluid container and has a plurality of through holes cut through top and bottom sides thereof and disposed in proximity to the top ends of the light guide tubes for the passing of the light beams from the light guide tubes.

Further, the fluid container can be made of a transparent or translucent material that admits light.

Further, the shell can be made of a transparent or translucent material that admits light.

Further, the light guide tubes can be made of a transparent or translucent material that admits light.

Further, each light guide tube has a diameter reducing in direction from the bottom end thereof that is attached to one light emitting device of the color light set toward the top end thereof that is kept in proximity to one through hole of the cover.

Further, the cover comprises an endless flange protruded from the bottom side thereof corresponding to the periphery of the oscillator for prohibiting splashing of the aromatic fluid during atomization of the aromatic fluid.

DETAILED DESCRIPTION OF THE PREFERRED EMBODIMENT

Figure 1:
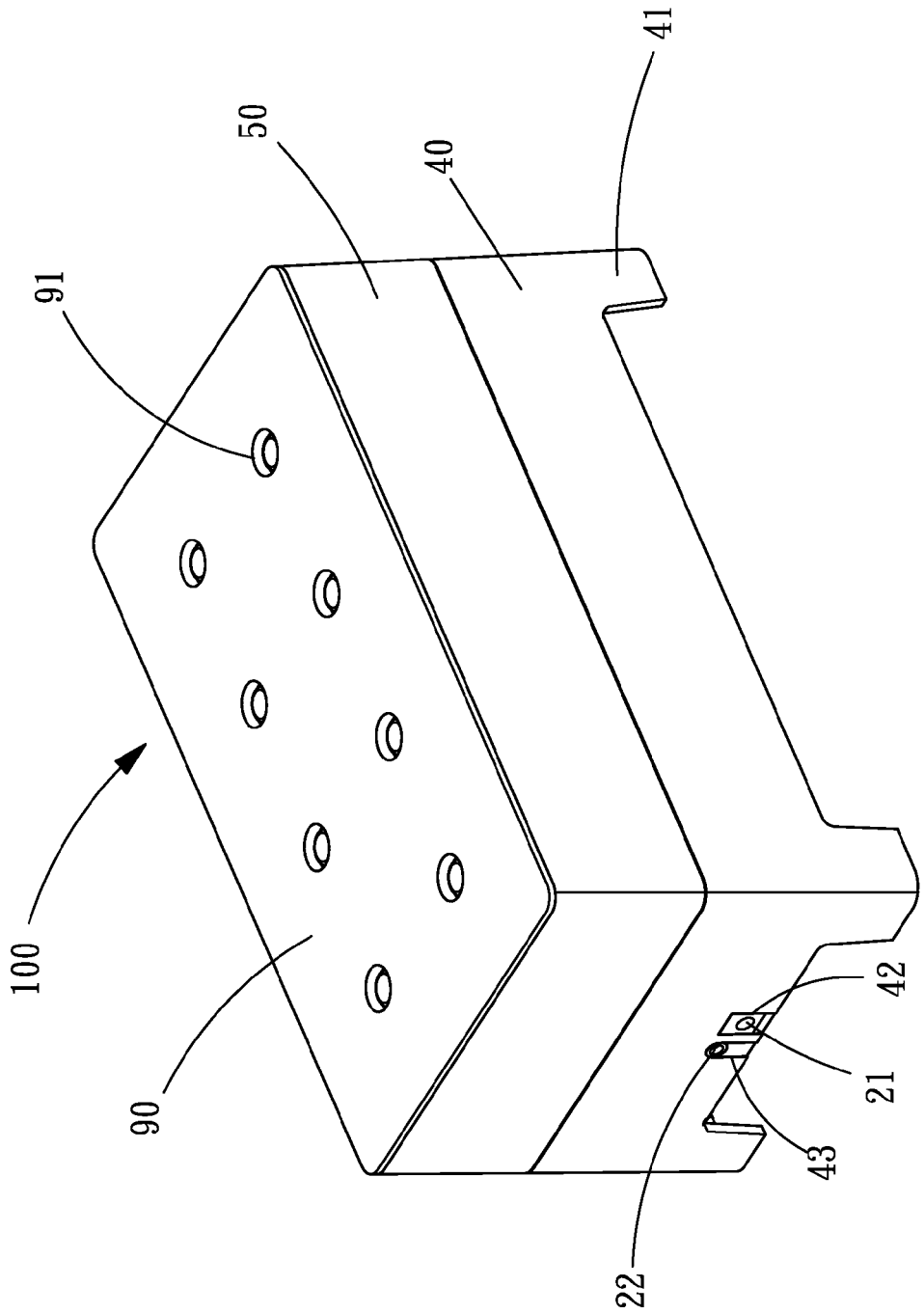
FIG. 1 is an elevational view of a combination aromatic nebulizing diffuser and color light set assembly in accordance with the present invention.

Referring to FIGS. 1~4, a combination aromatic nebulizing diffuser and color light set assembly 100 in accordance with the present invention is shown comprising a base panel 10, a power adapter 21, two electric fans 30, a shell 40, a fluid container 50, a color light set 60, an oscillator 70, a plurality of light guide tubes 80 and a cover 90.

Figure 2:
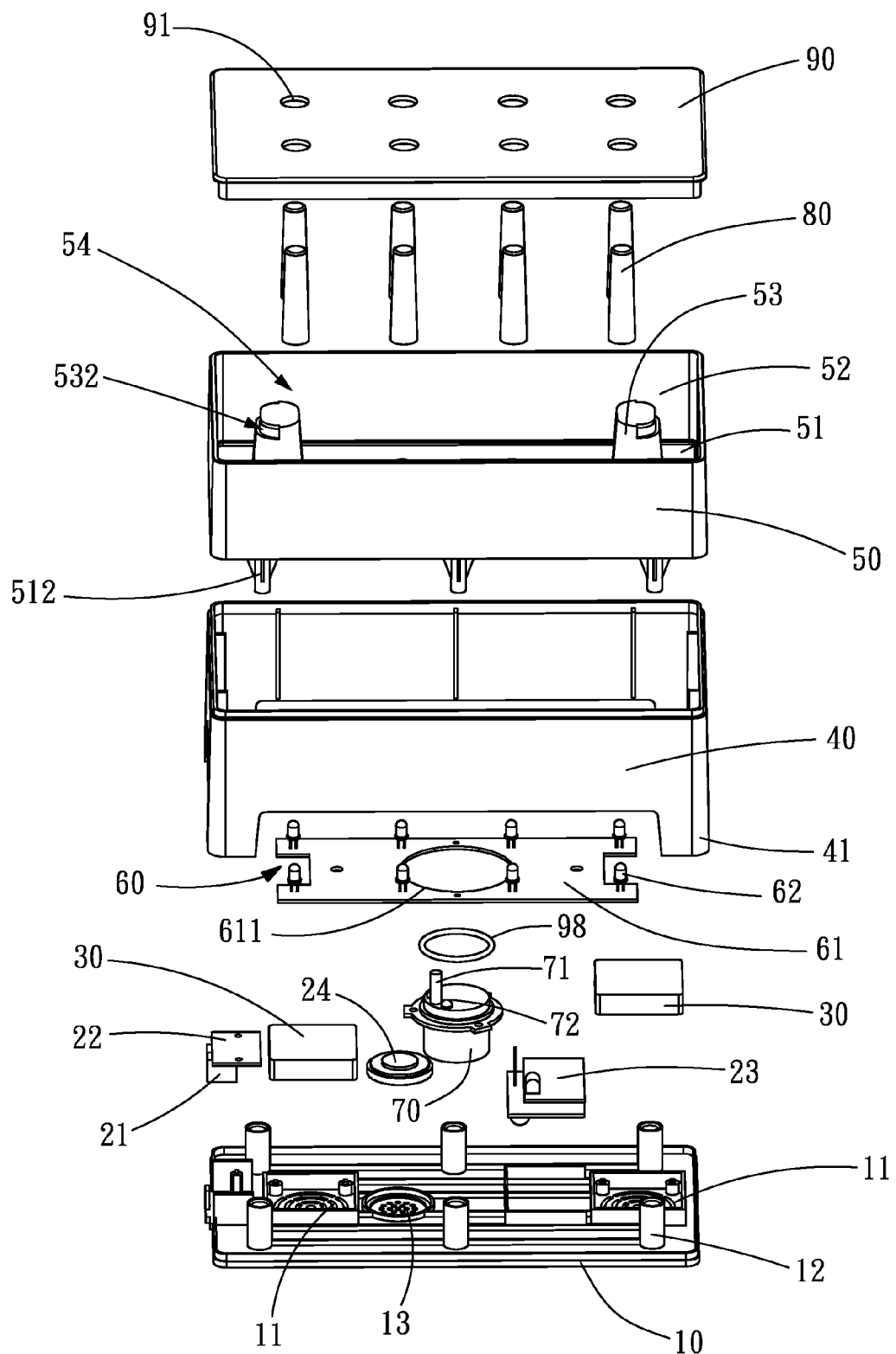
FIG. 2 is an exploded view of the combination aromatic nebulizing diffuser and color light set assembly in accordance with the present invention.
Figure 3:
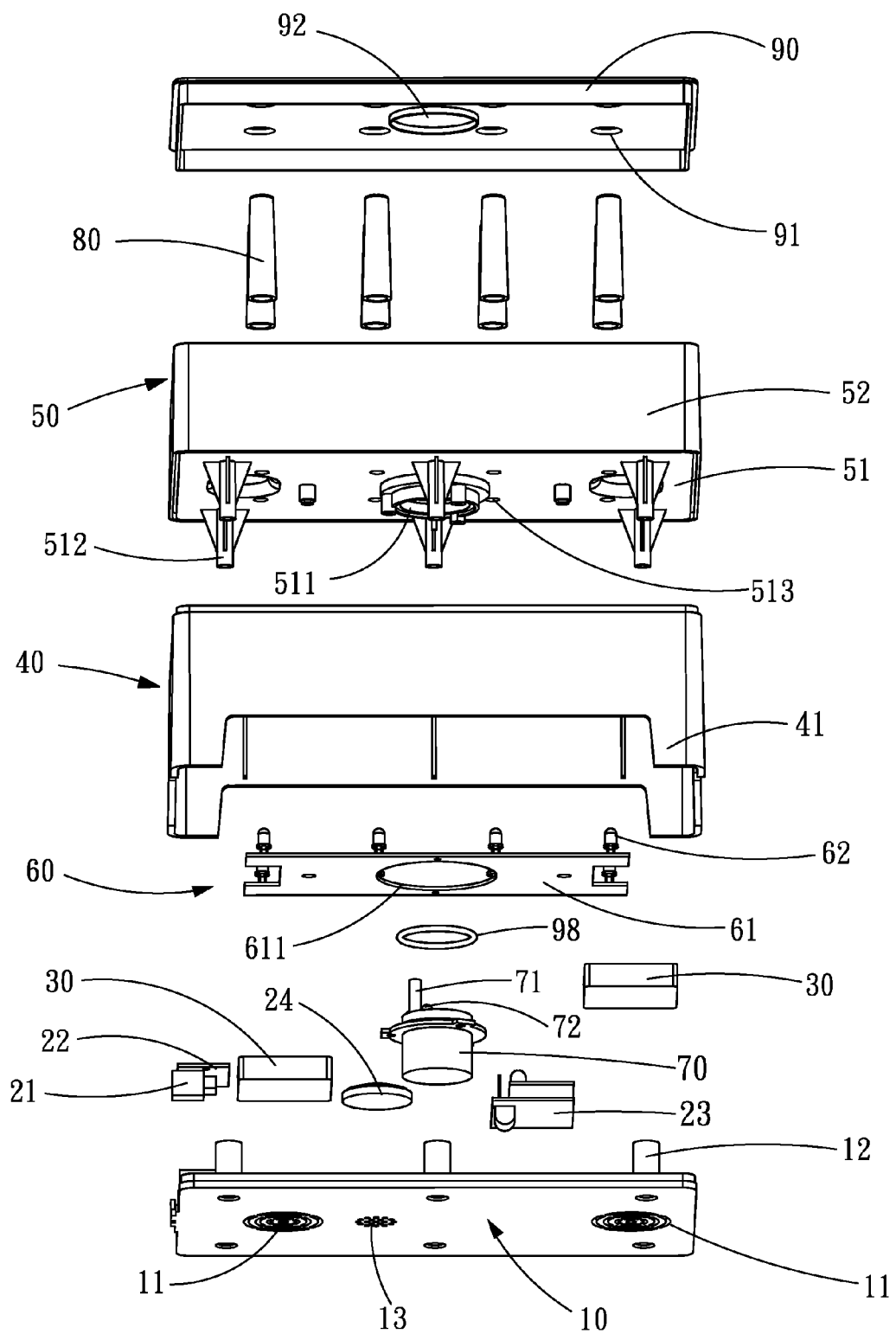
FIG. 3 corresponds to FIG. 1 when viewed from another angle.
Figure 4:
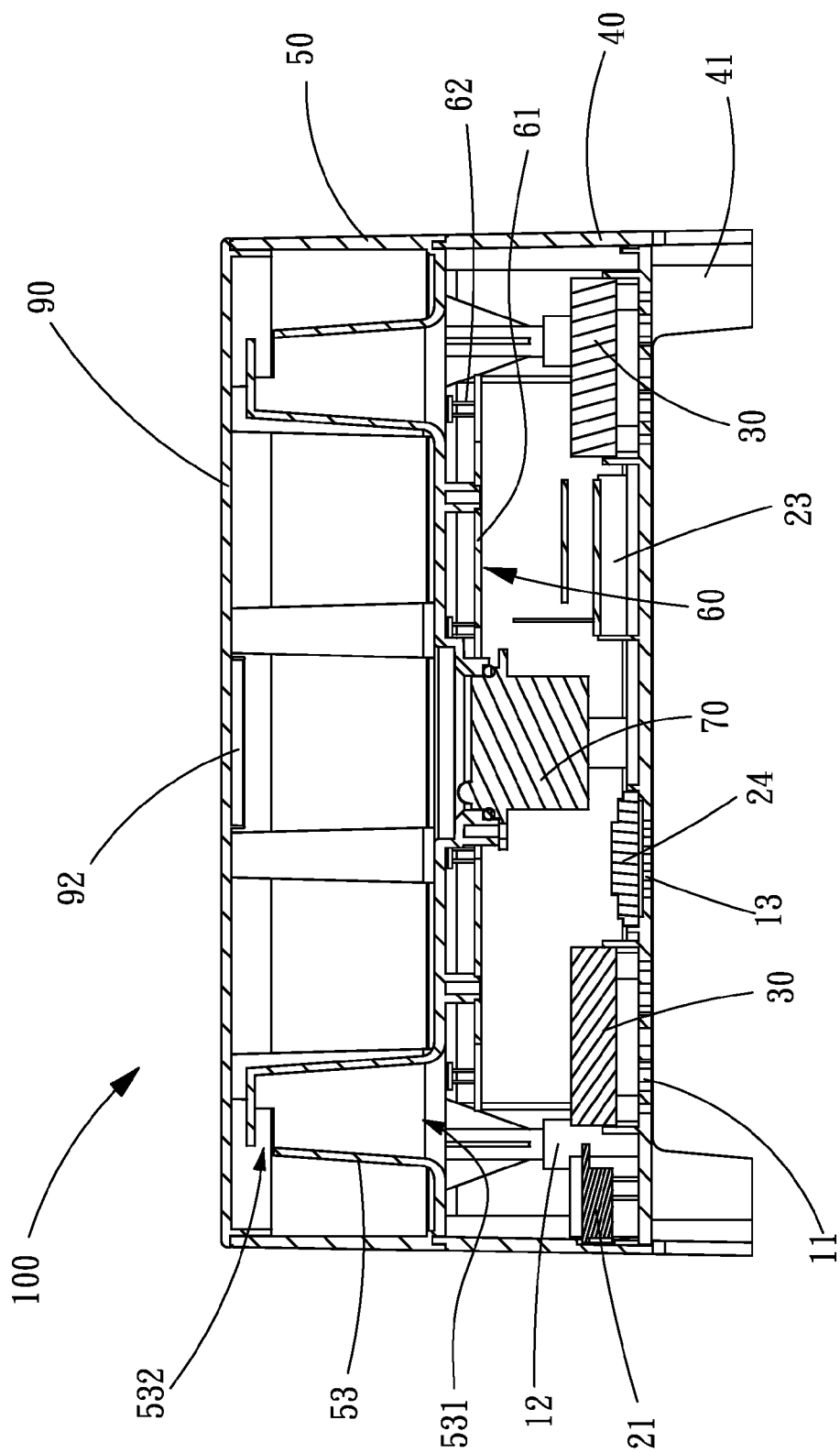
FIG. 4 is a sectional view of the combination aromatic nebulizing diffuser and color light set assembly shown in FIG. 1.

Referring to FIGS. 2~4 again, the base panel 10 defines two fan mounting zones and a power adapter mounting zone. Further, the base panel 10 comprises a plurality of air vents 11 cut through the top and bottom wall in each of the two fan mounting zones, and a plurality of upright support tubes 12 perpendicularly upwardly extended from the top wall.

Referring to FIGS. 2~4 again, the power adapter 21 is mounted in the base panel 10 within the power adapter mounting zone for the connection of an external power cable (not shown) for the input of an external power source.

Referring to FIGS. 2~4 again, the two electric fans 30 are respectively mounted on the top wall of the base panel 10 in each of the two fan mounting zones and electrically connected with the power adapter 21 to obtain the necessary working voltage from the power adapter 21. When the electric fans 30 are started, outside fresh air is drawn through the air vents 11 into the inside of the combination aromatic nebulizing diffuser and color light set assembly 100.

Referring to FIGS. 1~4, the shell 40 is shaped like a hollow rectangular box, having four legs 41 respectively downwardly extended from the bottom side in four corners for positioning on a flat surface stably.

Referring to FIGS. 2 and 3, the fluid container 50 comprises a bottom wall 51, an upright peripheral wall 52 upwardly extended from the border of the bottom wall 51, a fluid chamber 54 surrounded by the bottom wall 51 and the upright peripheral wall 52 and two air conduits 53 suspending in the fluid chamber 54, a center opening 511 cut through the bottom wall 51 in communication between the fluid chamber 54 and the outside space, and a plurality of through holes 513 cut through the bottom wall 51 around the center opening 511. Each air conduit 53 has an air inlet 531 and an air outlet 532. The air outlet 532 is kept in air communication with the inside space of the fluid chamber 54. The air inlet 531 faces one electric fan 30. Further, the bottom wall 51 of the fluid container 50 is supported on the top wall of the shell 40. The base panel 10 is fastened to the bottom wall of the shell 40. The fluid container 50, the base panel 10 and the shell 40 are fixedly fastened together, keeping the air inlets 531 of the air conduits 53 in alignment with the electric fans 30 respectively.

Referring to FIGS. 2~4, the color light set 60 comprises a circuit board 61 and a plurality of color light emitting devices 62 installed in the circuit board 61. The circuit board 61 is fixedly attached to the bottom (outer) surface of the bottom wall 51 of the fluid container 50 and electrically connected to the power adapter 21. The color light emitting devices 62 are respectively inserted through the through holes 513 into the inside of the fluid chamber 54.

Referring to FIGS. 2~4, the oscillator 70 according to the present preferred embodiment is an ultrasonic oscillator mounted in the center opening 511 at the center of the bottom wall 51 of the fluid container 50 and electrically connected to the power adapter 21 to obtain the necessary working voltage from the power adapter 21.

Referring to FIGS. 2~4, the light guide tubes 80 are vertically positioned in the fluid chamber 54 of the fluid container 50 with one ends thereof respectively surrounding the color light emitting devices 62 in the through holes 513.

Referring to FIGS. 1~4, the cover 90 is covered on the fluid container 50, having a plurality of through holes 91 cut through the top and bottom walls thereof at locations corresponding to the light guide tubes 80 and kept in proximity to the topmost edge of each of the light guide tubes 80 for output of the generated fine mist of atomized aromatic fluid molecules. The cover 90 further comprises an annular flange 92 downwardly protruded from the bottom wall thereof at the center corresponding to the center opening 511 of the fluid container 50 for stopping the generated fine mist of atomized aromatic fluid molecules from diffusion in horizontal direction and prohibiting splashing of the aromatic fluid during atomization.

After understanding of the structural features of the component parts of the combination aromatic nebulizing diffuser and color light set assembly 100 and their mounting arrangement, the application of the combination aromatic nebulizing diffuser and color light set assembly 100 is described hereinafter.

When in use, pour an aromatic fluid (for example, the mixture of an essential oil and water) into the fluid chamber 54 of the fluid container 50, and then start the oscillator 70 to generate an ultrasonic energy for causing atomization of aromatic fluid. At this time, the electric fans 30 are started to draw in outside fresh air. The intake flow of air goes through the air inlets 531 and air outlets 532 of the air conduits 53 into the inside space of the fluid chamber 54 to carry the generated fine mist of atomized aromatic fluid molecules through the through holes 91 of the cover 90 to the outside space. At the same time, the light guide tubes 80 condense the color light from the color light emitting devices 62 into color light beams, producing a visual effect.

Figure 5:
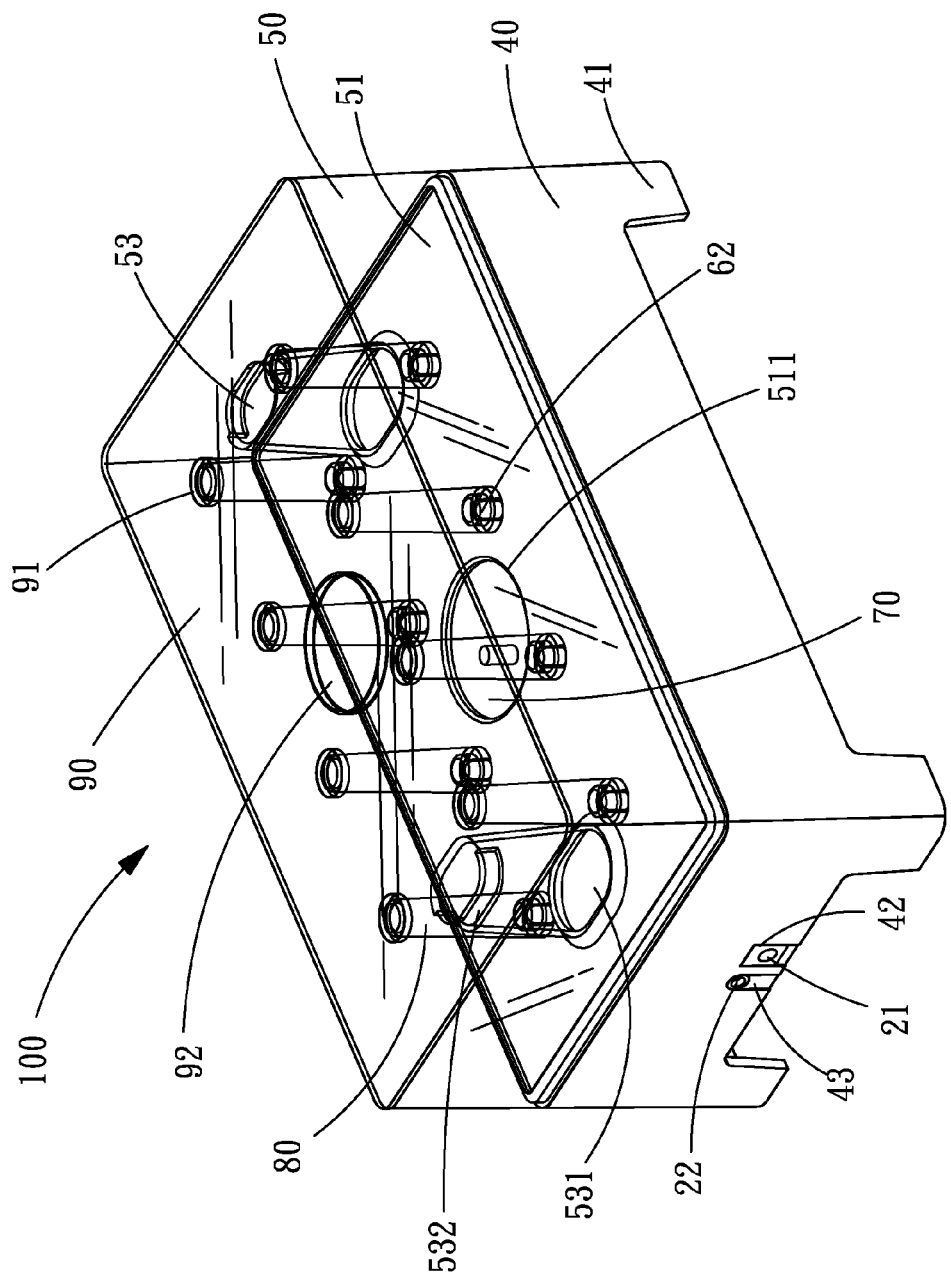
FIG. 5 is a perspective view of the combination aromatic nebulizing diffuser and color light set assembly shown in FIG. 1.

Referring to FIGS. 4 and 5, each air conduit 53 has an inner diameter gradually reducing in direction from the air inlet 531 toward the air outlet 532. When the induced current of air goes through one air conduit 53, the speed of the induced current of air is accelerated. Therefore, the air currents that go out of the air conduits 53 carry the generated fine mist of atomized aromatic fluid molecules through the through holes 91 of the cover 90 to the outside space efficiently.

During oscillation of the oscillator 70 in the aromatic fluid in the fluid chamber 54 of the fluid container 50, the annular flange 92 prohibits horizontal diffusion of the generated fine mist of atomized aromatic fluid molecules, enabling the generated fine mist of atomized aromatic fluid molecules to be carried by the induced currents of air from the fluid chamber 54 through the through holes 91 of the cover 90 to the outside space efficiently.

Further, each color light emitting device 62 of the color light set 60 can be comprised of a red light emitting diode chip, a blue light emitting diode chip, a green light emitting diode chip, or the combination of a red light emitting diode chip, a blue light emitting diode chip and a green light emitting diode chip. Subject to the control of the circuit board 61, the color light emitting devices 62 emit mixed colors of light. The light guide tubes 80 condense the mixed colors of light into color light beams that go through the through holes 91 of the cover 90 to the outside space to illuminate the fine mist of atomized aromatic fluid molecules being carried out of the combination aromatic nebulizing diffuser and color light set assembly 100 by the induced currents of air.

Further, the circuit board 71 of the color light set 60 has an opening 611 for accommodating the oscillator 70.

Referring to FIGS. 1 and 2, the shell 40 has a power adapter hole 42 located on one lateral side thereof for receiving a part of power adapter 21 so that an external power cable (not shown) can be conveniently connected to the power adapter 21.

Referring to FIG. 5, the fluid container 50 and the cover 90 can be prepared from a transparent material, translucent material, or any of a variety of other materials that admit light, such as glass, ceramics, frosted glass, acrylic, plastics or crystal. Further, the fluid container 50 and the cover 90 can be made in any desired color. Thus, people can see through the combination aromatic nebulizing diffuser and color light set assembly 100, viewing the floating of the generated fine mist of atomized aromatic fluid molecules and the presence of the mixed color of lights in the fluid container 50.

Further, the aforesaid light guide tubes 80 can be prepared from glass, frosted glass, acrylic, plastics or crystal in any desired color for guiding the colors of light emitted from the light emitting devices 62 out of the fluid container 50 and the cover 90 in beams.

Further, the aforesaid light guide tubes 80 are preferably tapered, having a diameter gradually reducing in direction from the through holes 513 of the fluid container 50 toward the through holes 91 of the cover 90. Therefore, the light guide tubes 80 effectively condense the colors of light emitted from the light emitting devices 62 into upwardly extending color light beams, producing visual lighting effects.

Referring to FIGS. 2~4, the oscillator 70 comprises a built-in control circuit that controls the oscillator 70 to oscillate in frequency about several million cycles per second. Further, the oscillator 70 is mounted in the center opening 511 on the bottom wall 51 of the fluid container 50 and sealed with a gasket ring 98 to prevent leakage.

Referring to FIGS. 2~4, the oscillator 70 carries a water lever sensor 71 and a light source 72. The water level sensor 71 is disposed in the fluid chamber 54 of the fluid container 50 and adapted to detect the level of the contained aromatic fluid. The light source 72 is controllable to emit light, thereby illuminating the fluid chamber 54. The built-in control circuit of the ultrasonic oscillator 70 controls the operation of the water lever sensor 71 and a light source 72. When the level of the aromatic fluid in the fluid chamber 54 is below a predetermined value, the control circuit of the ultrasonic oscillator 70 cuts off power supply from the ultrasonic oscillator 70, preventing damage. Further, the light source 72 can be comprised of at least one LED component adapted for emitting a predetermined color of light.

The aforesaid fluid container 50 further comprises a plurality of bottom mounting rods 512 downwardly extended from the bottom wall 51; the base panel 10 comprises a plurality of upright mounting tubes 12 for receiving the bottom mounting rods 512 of the fluid container 50. Thus, the base panel 10 can be detachably fastened to the fluid container 50, facilitating cleaning.

Further, after plugging the bottom mounting rods 512 of the fluid container 50 into the upright mounting tubes 12 of the base panel 10, screws (not shown) may be installed to affix the base panel 10 to the fluid container 50.

The combination aromatic nebulizing diffuser and color light set assembly 100 further comprises an audio source input connector 22 mounted on the base panel 10 for the connection of an external sound source, for example, a music player or multimedia storage device (not shown) for sound source input.

The combination aromatic nebulizing diffuser and color light set assembly 100 further comprises a music control circuit board 23 mounted on the base panel 10 and electrically connected to the power adapter 21, having storage means for storing natural voices, music files, animal sounds or the like.

The combination aromatic nebulizing diffuser and color light set assembly 100 further comprises a speaker 24 mounted on the base panel 10 above sound holes 13 on the base panel 10 and electrically connected to the audio source input connector 22 and the music control circuit board 23 to convert an electrical signal from the audio source input connector 22 or the music control circuit board 23 into sound that is driven out of the combination aromatic nebulizing diffuser and color light set assembly 100 through the sound holes 13 of the base panel 10. Therefore, sound and lighting effects are created during operation of the combination aromatic nebulizing diffuser and color light set assembly 100. Further, the shell 40 shields the speaker 24, the electric fans 30 and the music control circuit board 23, enabling the audio source input connector 22 to be partially mounted in an audio source connector mounting through hole 43 on the shell 40 for the connection of external sound source means.

A prototype of combination aromatic nebulizing diffuser and color light set assembly has been constructed with the features of FIGS. 1~5. The combination aromatic nebulizing diffuser and color light set assembly functions smoothly to provide all of the features disclosed earlier.

Although a particular embodiment of the invention has been described in detail for purposes of illustration, various modifications and enhancements may be made without departing from the spirit and scope of the invention. Accordingly, the invention is not to be limited except as by the appended claims.

What is the invention claimed is:

1. An combination aromatic nebulizing diffuser and color light set assembly, comprising:

a base panel, said base panel comprising a plurality of air vents cut through top and bottom sides thereof;

at least one electric fan mounted on the top side of said base panel corresponding to said air vents for drawing in outside air;

a fluid container, said fluid container comprising a bottom wall, an upright peripheral wall, a fluid chamber surrounded by said bottom wall and said upright peripheral wall for holding an aromatic fluid, at least one air conduit suspending in said fluid chamber, each said air conduit having an air inlet facing one said electric fan for guiding in currents of air from the associating electric fan and an air outlet in air communication with the space in said fluid chamber of said fluid container above the aromatic fluid contained in said fluid chamber, an opening cut through said bottom wall and a plurality of through holes cut through said bottom wall;

an oscillator mounted in the opening of said fluid chamber for generating an oscillating energy to cause automation of the aromatic fluid being held in said fluid chamber;

a color light set, said color light set comprising a circuit board affixed to the bottom wall of said fluid container and a plurality of light emitting devices electrically connected to said circuit board and respectively mounted in the through holes on the bottom wall of said fluid container;

a power adapter mounted on said base panel and electrically connected with said at least one electric fan and said oscillator and said circuit board of said color light set to provide the necessary working voltage to said at least one electric fan, said oscillator and said color light set;

a shell for supporting said fluid container on a flat surface, said shell comprising a top edge stopped against the bottom wall of said fluid container and a plurality of legs downwardly extended from a bottom side thereof in four corners for positioning on a flat surface;

a plurality of light guide tubes vertically positioned in said fluid chamber of said fluid container and adapted to condense emitted light from said light emitting devices into a respective light beam, each said light guide tube having a bottom end surrounding one said light emitting device and a top end opposite to the bottom end; and a cover covering said fluid container, said cover comprising a plurality of through holes cut through top and bottom sides thereof and disposed in proximity to the top ends of said light guide tubes for the passing of the light beams from said light guide tubes.

2. The combination aromatic nebulizing diffuser and color light set assembly as claimed in claim 1, wherein said base panel has carried thereon a speaker, a music control circuit board and an audio source input connector, said speaker being electrically connected with said music control circuit board and said audio source input connector, said music control circuit board being electrically connected with said power adapter, said audio source input connector being electrically connected with said music control circuit board; said base panel comprises a plurality of sound holes cut through the top and bottom sides thereof for guiding out sound waves from said speaker; said shell comprises a power adapter hole and an audio source connector mounting through hole cut through a peripheral wall thereof for accommodating said power adapter and said audio source connector respectively.

3. The combination aromatic nebulizing diffuser and color light set assembly as claimed in claim 1, wherein said fluid container and said shell admit light.

4. The combination aromatic nebulizing diffuser and color light set assembly as claimed in claim 1, wherein said base panel comprises a plurality of upright mounting tubes; said fluid container comprises a plurality of bottom mounting rods downwardly extended from the bottom wall thereof and respectively plugged into the upright mounting tubes of said base panel.

5. The combination aromatic nebulizing diffuser and color light set assembly as claimed in claim 1, wherein said light guide tubes admit light.

6. The combination aromatic nebulizing diffuser and color light set assembly as claimed in claim 1, wherein said oscillator carries a water level sensor adapted for detecting the level of the aromatic fluid held in said fluid chamber and a light emitting device adapted for emitting light toward the inside of said fluid chamber.

7. The combination aromatic nebulizing diffuser and color light set assembly as claimed in claim 1, wherein each said light emitting device of said color light set comprises at least one of a red light emitting diode chip, a blue light emitting diode chip, a green light emitting diode chip and the combination of a red light emitting diode chip, a blue light emitting diode chip and a green light emitting diode chip.

8. The combination aromatic nebulizing diffuser and color light set assembly as claimed in claim 1, wherein each said light guide tube has a diameter reducing in direction from the bottom end thereof toward the top end thereof.

9. The combination aromatic nebulizing diffuser and color light set assembly as claimed in claim 1, wherein each said air conduit has a diameter reducing in direction from the air inlet thereof toward the air outlet thereof.

10. The combination aromatic nebulizing diffuser and color light set assembly as claimed in claim 1, wherein said cover comprises an endless flange protruded from the bottom side thereof corresponding to the periphery of said oscillator.

* * * * *